(12) United States Patent
Dible

(10) Patent No.: US 6,222,718 B1
(45) Date of Patent: Apr. 24, 2001

(54) INTEGRATED POWER MODULES FOR PLASMA PROCESSING SYSTEMS

(75) Inventor: Robert D. Dible, Fremont, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 09/191,151

(22) Filed: Nov. 12, 1998

(51) Int. Cl.[7] .................................................. H02H 23/00
(52) U.S. Cl. ............................................. 361/234; 361/601
(58) Field of Search ............................. 361/62, 110, 234, 361/235, 661, 728, 729, 730; 307/18–22, 25, 26, 43, 84, 147; 438/19, 907, 908; 56/379.6

(56) References Cited

U.S. PATENT DOCUMENTS

| | | | |
|---|---|---|---|
| 5,236,512 | 8/1993 | Rogers et al. | 134/1 |
| 5,633,502 | 5/1997 | Fischione | 250/441.11 |
| 5,637,961 | 6/1997 | Ishii et al. | 315/111.51 |
| 5,737,175 | * 4/1998 | Grosshart et al. | 361/234 |
| 5,784,238 | 7/1998 | Nering et al. | 361/65 |

FOREIGN PATENT DOCUMENTS

0517042A1 12/1992 (EP) .............................. C23C/16/48

OTHER PUBLICATIONS

International Search Report dated Feb. 10, 2000.

* cited by examiner

Primary Examiner—Ronald W. Leja
(74) Attorney, Agent, or Firm—Beyer Weaver & Thomas, LLP

(57) ABSTRACT

A power delivery system for providing energy to sustain a plasma in a plasma processing chamber configured for processing substrates. The power delivery system includes a metallic enclosure having an input port, a first output port, a second output port, and a third output port. There is further included a power distribution box disposed within the enclosure. The power distribution box includes a first AC input port for receiving AC power from external of the metallic enclosure through the input port and for providing AC power to AC loads external to the metallic enclosure via the first output port. There is also included a DC power supply electrically coupled to the power distribution box. The DC power supply is configured to receive the AC power from the power distribution box and to output DC power. The DC power supply is disposed within the metallic enclosure. The DC power is supplied to DC loads external of the metallic enclosure via the second output port. Additionally, there is included a first RF generator electrically coupled to the power distribution box to receive the AC power. The first RF generator is coupled with the DC power supply to receive the DC power. The first RF generator is disposed within the metallic enclosure. Further, there is included a first match network electrically coupled with an output of the first RF generator to receive RF energy from the first RF generator. The first match network has a first match network output for providing first matched RF energy to a first electrode of the plasma processing chamber via the third output port. The first match network is disposed within the metallic enclosure, wherein no other RF generator associated with the plasma processing chamber exists outside the metallic enclosure.

30 Claims, 5 Drawing Sheets

INTEGRATED POWER MODULES FOR PLASMA PROCESSING SYSTEMS

BACKGROUND OF THE INVENTION

The present invention relates to plasma processing systems for use in the manufacture of semiconductor integrated circuits. More particularly, the present invention relates to improved plasma processing system IPMs (integrated power modules) that offer improved reliability and lower acquisition/maintenance costs.

Plasma processing systems have long been employed in the manufacture of semiconductor devices (such as integrated circuits or flat panel displays). In a typical plasma processing system, the substrate (e.g., the wafer or the glass panel) is typically disposed inside a plasma processing chamber for processing. Energy in the form of AC, DC, RF, or microwave is then delivered to the plasma processing chamber to form a plasma out of supplied etchant or deposition source gases. The plasma may then be employed to deposit a layer of material onto the surface of the substrate or to etch the substrate surface.

As the electrodes require energy to ignite and sustain the plasma, a power delivery system is typically required to condition the AC power obtained from the grid, to transform the AC power into the appropriate form of energy required to ignite and sustain the plasma, and to provide the DC voltages for operating the control electronics.

To facilitate discussion, FIG. 1 illustrates a simplified power delivery system of a currently available plasma processing system known as the 4520XL™, available from Lam Research Corporation of Fremont, Calif. In the example of FIG. 1, plasma processing system 100 represents a parallel plate, multiple frequencies plasma processing system. It should be appreciated, however, that the discussion herein is not limited to this specific type of plasma processing system. In fact, the concept discussed herein is applicable to plasma processing systems in general irrespective of the number of electrodes, the geometry of the chamber, or the type of energy source employed. Further, although only one chamber of plasma processing system 100 is shown to facilitate discussion, it should be appreciated that a plasma processing system may take the form of a cluster tool, which may include one or multiple modules, each of which may have one or multiple chambers per module.

Referring now to FIG. 1, wafer 102 is shown disposed in a plasma processing chamber 104 for processing. More specifically, wafer 102 is shown disposed on a chuck 106, which acts as one electrode. The other electrode 108 is disposed above wafer 102 as shown. RF generator 110 represents a 27 MHz RF generator, which supplies RF energy to match a network 114 through a coax cable 122. As is well known, one function of the match network is to match the impedance of the plasma to that of the generator in order to maximize power delivery. From match network 114, the RF energy is provided to electrode 108 through a diplexer 118. A diplexer is a well known device that passes energy of a certain frequency while passing energy having other frequencies to ground. Since electrode 108 is a 27 MHz electrode, diplexer 118 passes 27 MHz RF energy to electrode 108 while passing RF energy having other frequencies to ground.

Likewise, RF generator 112 represents a 2 MHz RF generator which supplies the RF energy to match network 116 through coax cable 124. From match network 116, the RF energy is supplied to a diplexer 120 through coax cable 126. Diplexer 120 passes 2 MHz RF energy to chuck 106 and passes RF energy having other frequencies directly to ground.

Nowadays, the various major functional blocks of a power delivery system (e.g., generators, matches, diplexers, or the like) are typically distributed among multiple subsystems, many of which are enclosed in their own EMI enclosures and include their own DC power supplies. This is because the current practice in power delivery system design is to render the major functional blocks or subsystems as modular as possible. In other words, the current practice is to provide each subsystem with sufficient local resources onboard (e.g., DC power supplies to operate the local electronics) so as to enable a given subsystem to be readily adapted for use in a plug-and-play fashion in many different plasma processing systems. By commoditizing these subsystems, the vendors of these subsystems hope to achieve economy of scale since fewer subsystems need to be designed and inventoried for the plasma processing equipment market.

There is also another design philosophy in the semiconductor processing equipment industry which favors the provision of resources required by each subsystem (e.g., DC power supplies) in the subsystems themselves. As plasma processing systems become more complex and expensive, lower cost of ownership is achieved by reducing the amount of time that the plasma processing system is out of service due to equipment failures. Beside improving the quality of the subsystems, vendors of plasma power delivery systems believe that by distributing the resources among the various modular subsystems, the effects of a subsystem failure can be isolated and addressed quickly. By making the subsystems modular and self-sufficient in terms of required resources, the failed subsystem can be swapped out, and the plasma processing system can be brought back into operation quickly.

As a practical matter, each of these modular subsystems (e.g., match networks 114 and 116, diplexers 118 and 120 and RF generators 110 and 112) occupies a nontrivial amount of space. Accordingly, it is oftentimes impractical to position these subsystems close to the plasma processing chamber and still provide adequate space for maintenance. The crowding problem is exacerbated in a cluster tool environment where multiple chambers may be positioned in close proximity to one another.

In the prior art, the crowding problem is addressed by moving certain subsystems to a remote location and to connect the subsystems together via conductors/or and coax cables. With reference to FIG. 1, for example, RF generators 110 and 112, along with their water cooling systems and control electronics, may be positioned away from the plasma processing chamber to relieve crowding. In the typical case, RF generators 110 and 112 may be installed on a rack some distance away (50–60 feet in some cases) from the plasma processing chamber. Other subsystems such as matches and/or diplexers may be located closer to chamber 104 within the assembly shown as plasma processing module 150. Coax cables 122 and 124 are then employed to couple the RF generators on rack 152 to the subsystems at plasma processing module 150.

Because the subsystems of the power delivery system are now split among multiple locations, separate power distribution boxes are required. With reference to FIG. 1, rack 152 requires a power distribution box 154 to receive AC power from the grid (e.g., in the form of 208 volts, 3-phase) and to distribute AC power to RF a generators 110 and 112 via conductors 156 and 158. These conductors 156 and 158 plug into RF generators 110 and 112, which are provided with complementary plugs for quick connection and disconnection. Generator 110 also includes an additional connector for connecting with coax cable 122 (which supplies the RF energy to match network 114). Likewise, RF generator 112 also includes an additional connector to couple with coax cable 124 (which supplies the RF energy to match network 116).

DC voltages to the control electronics within RF generators 110 and 112 are provided by DC generators, which are typically provided onboard each RF generator to satisfy modular design guidelines. In the example of FIG. 1, RF generator 110 is shown having a DC power supply 162 for converting the AC voltage received at RF generator 110 to the DC voltages levels required by its control electronics. Likewise, RF generator 112 is shown having a DC power supply 164 for converting the AC voltage received at RF generator 112 to the DC voltage levels required by its control electronics. If other sensors or control electronics external to the generators exist on rack 152, additional DC power supplies may be provided on rack 152. For safety, rack 152 typically comes with an EMO (Emergency Off) subsystem 160, which is essentially a panic switch that allows AC power to be shut off quickly in case of emergency.

Since plasma processing module 150 is remoted from rack 152, a separate power distribution box is now required for plasma processing module 150. This power distribution box is shown as power distribution box 170, which includes its own separate DC power supply 172 to provide the requisite DC voltages to the control electronics local to plasma processing module 150. Like power distribution box 154, power distribution box 170 includes the contactors, relays, and connectors required to provide AC power to the various AC loads of plasma processing module 150 such as the pumps, heaters, and the like. Conductors from DC power supply 172 lead to various control electronics (including those on the chamber and in the match networks), sensors, and other DC loads within plasma processing module 150. For safety reasons, an EMO (Emergency Off) subsystem 174 is provided with plasma processing module 150 to permit power to the subsystems of plasma processing module 150 to be shut off in an emergency.

It has been recognized by the inventor herein that the current power delivery system has certain disadvantages. By way of example, the attempt to turn each major functional block of the power delivery system (such as generators, matches, diplexers, or the like) into a modular, stand-alone subsystem introduces unnecessary redundancy of components into the assembled power delivery system. This is because there are multiple DC power supplies, EMO subsystems, power distribution boxes, power line filters, relays, connectors, contactors, coax cables, conductors in the power delivery system after it is assembled from the modular subsystems. The high component count of the assembled power delivery system disadvantageously increases the acquisition cost.

Ironically, the redundancy of components does not increase reliability since when a component fails, the subsystem affected would still bring down the entire plasma processing system since these redundant components exist in different subsystems and do not serve as backups for one another. In fact, the high component count decreases reliability since there are now more components to fail.

As mentioned earlier, the attempt to modularize the major functional blocks of the power delivery subsystem also renders it difficult to package these subsystems, each with its own bulky EMI enclosure, within the tight space available around each plasma processing chamber. When certain subsystems are positioned away from the plasma processing chamber to relieve crowding, long coax cables and conductors are required, which introduces losses into the power delivery system and increases EMI concerns. The use of coax cables and coax connectors for providing high voltage/high current signals between the various subsystems (e.g., between an RF generator and its match network) also decreases reliability. This is because the coax cables and/or the connectors tend to break down over time when they are required to carry high voltage/high current signals.

In view of the foregoing, there are desired improved power delivery systems for providing power to ignite or sustain plasma in a plasma processing chamber.

SUMMARY OF THE INVENTION

The invention relates, in one embodiment, to a power delivery system for providing energy to sustain a plasma in a plasma processing chamber configured for processing substrates. The power delivery system includes a metallic enclosure having an input port, a first output port, a second output port, and a third output port. There is further included a power distribution box disposed within the enclosure. The power distribution box includes a first AC input port for receiving AC power from external of the metallic enclosure through the input port and for providing AC power to AC loads external to the metallic enclosure via the first output port. There is also included a DC power supply electrically coupled to the power distribution box. The DC power supply is configured to receive the AC power from the power distribution box and to output DC power. The DC power supply is disposed within the metallic enclosure. The DC power is supplied to DC loads external of the metallic enclosure via the second output port.

Additionally, there is included a first RF generator electrically coupled to the power distribution box to receive the AC power. The first RF generator is coupled with the DC power supply to receive the DC power. The first RF generator is disposed within the metallic enclosure. Further, there is included a first match network electrically coupled with an output of the first RF generator to receive RF energy from the first RF generator. The first match network has a first match network output for providing first matched RF energy to a first electrode of the plasma processing chamber via the third output port. The first match network is disposed within the metallic enclosure, wherein no other RF generator associated with the plasma processing chamber exists outside the metallic enclosure.

In another embodiment, the invention relates to a method for providing energy to sustain plasma in a plasma processing chamber configured for processing substrates. The method includes providing a metallic enclosure having an input port, a first output port, a second output port, and a third output port. The method further includes placing a power distribution box within the enclosure. The power distribution box includes a first AC input port for receiving AC power from external of the metallic enclosure through the input port and for providing AC power to AC loads external to the metallic enclosure via the first output port. The method further includes electrically coupling a DC power supply to the power distribution box. The DC power supply is configured to receive the AC power from the power distribution box and to output DC power. The DC power supply is disposed within the metallic enclosure. The DC power is supplied to DC loads external of the metallic enclosure via the second output port.

The method additionally includes electrically coupling a first RF generator to the power distribution box to receive the AC power. The first RF generator is coupled with the DC power supply to receive the DC power. The first RF generator is disposed within the metallic enclosure. Furthermore, the method includes electrically coupling a first match network with an output of the first RF generator to receive RF energy from the first RF generator. The first match network has a first match network output for providing first matched RF energy to the electrode via the third output port. The first match network is disposed within the metallic enclosure, wherein no other RF generator associated with the plasma processing chamber exists outside the metallic enclosure.

These and other advantages of the present invention will become apparent upon reading the following detailed descriptions and studying the various drawings.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

Figure 1:
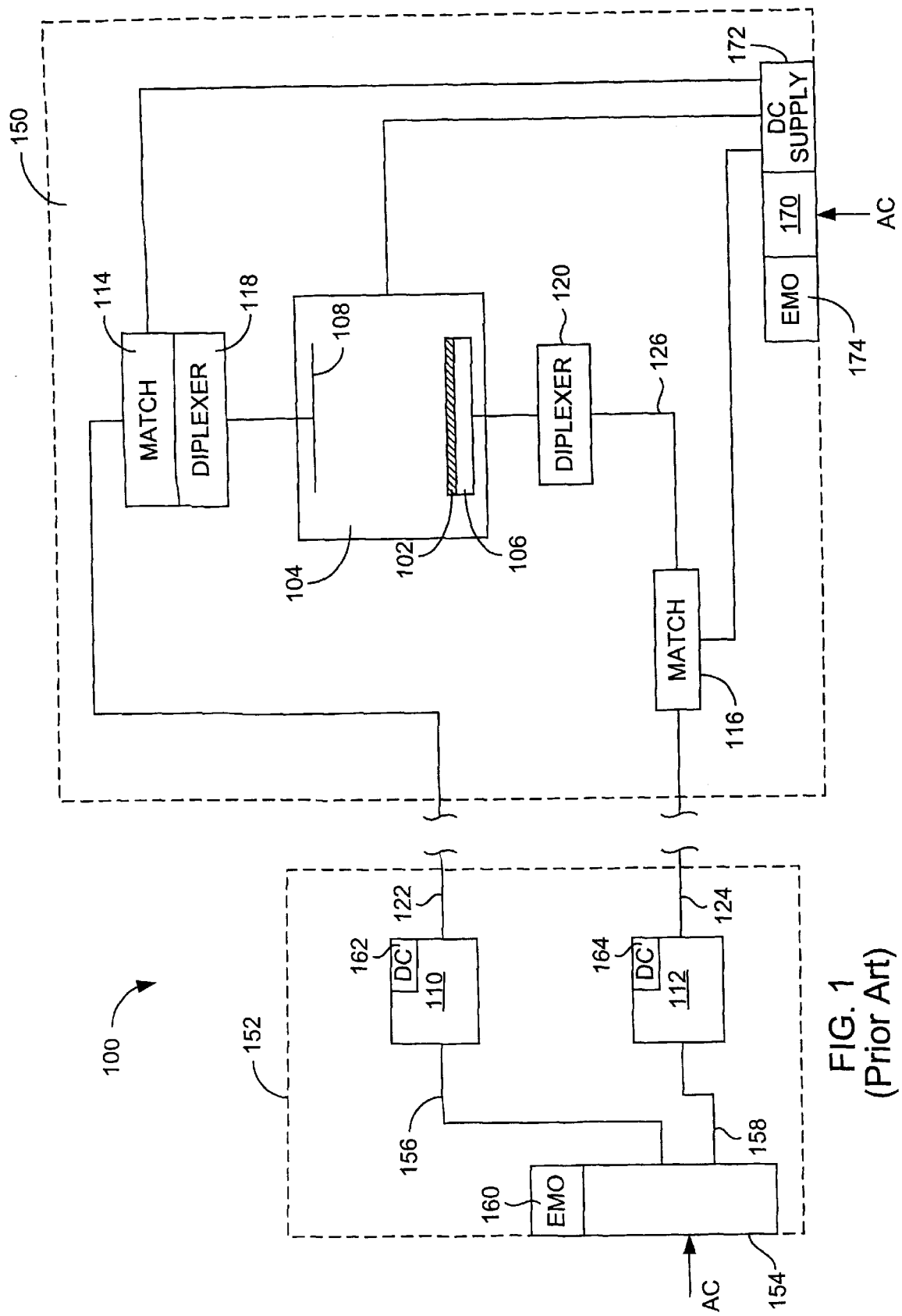
FIG. 1 illustrates a prior art power delivery system for a parallel plate plasma processing system.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to avoid unnecessarily obscuring the present invention.

In accordance with one aspect of the present invention, the footprint of the assembled power delivery system may be substantially reduced by removing redundant components from the major functional blocks of the power delivery system, which redundant components were provided to accommodate the contemporary modular design philosophy. Furthermore, the separate EMI enclosures that were provided with the modular, stand-alone subsystems are also eliminated to reduce the bulkiness of the assembled power delivery system. To provide EMI shielding, the major functional blocks of the power delivery system are instead grouped together into an integrated power module (IPM) and enclosed in a single system-level EMI enclosure (e.g., a metallic enclosure). The close proximity of the subsystems is made possible by removing both the redundant components and the separate EMI enclosures. By grouping the subsystems in close proximity to one another and containing the subsystems of the power delivery system in one system-level EMI enclosure, long coax cables are no longer required to couple the subsystems (e.g., the RF generators and the matched networks) together.

Because of the use of the system-level EMI enclosure, which would have been impractical had the major functional blocks of the power delivery system been remoted from one another, the electrical connections between the subsystems may now be made with simple conductors and straps. This would not have been possible had the subsystems been remoted from one another since these conductors and straps do not meet EMI shielding requirements unless enclosed in an EMI enclosure. Since the subsystems and the electrical connections therebetween are now enclosed in the system-level EMI enclosure, the electrical connections themselves do not have to meet the EMI shielding requirements of exposed conductors and connectors. In this manner, the reliability problem associated with the use of coax cables and coax connectors for carrying high voltage/high current signals is substantially alleviated. By placing the subsystems closer together within the EMI enclosure, power losses attributed to the use of long coax cables are also substantially minimized.

Most importantly, the elimination of the redundant components, which were necessitated by the modular design philosophy of prior art power delivery systems, reduces the component count in the assembled power delivery system. With the component count reduced, the acquisition cost of the entire power delivery system is reduced. Further, the reduction in the component count also improves reliability since there are fewer components to fail. Since the entire power delivery system is now smaller, if one of the components fails, the entire integrated power module may be swapped out in the same manner that individual subsystems were swapped out in the prior art example of FIG. 1. Accordingly, the plasma processing system may be brought back into production quickly, advantageously reducing the cost of ownership.

Figure 2:
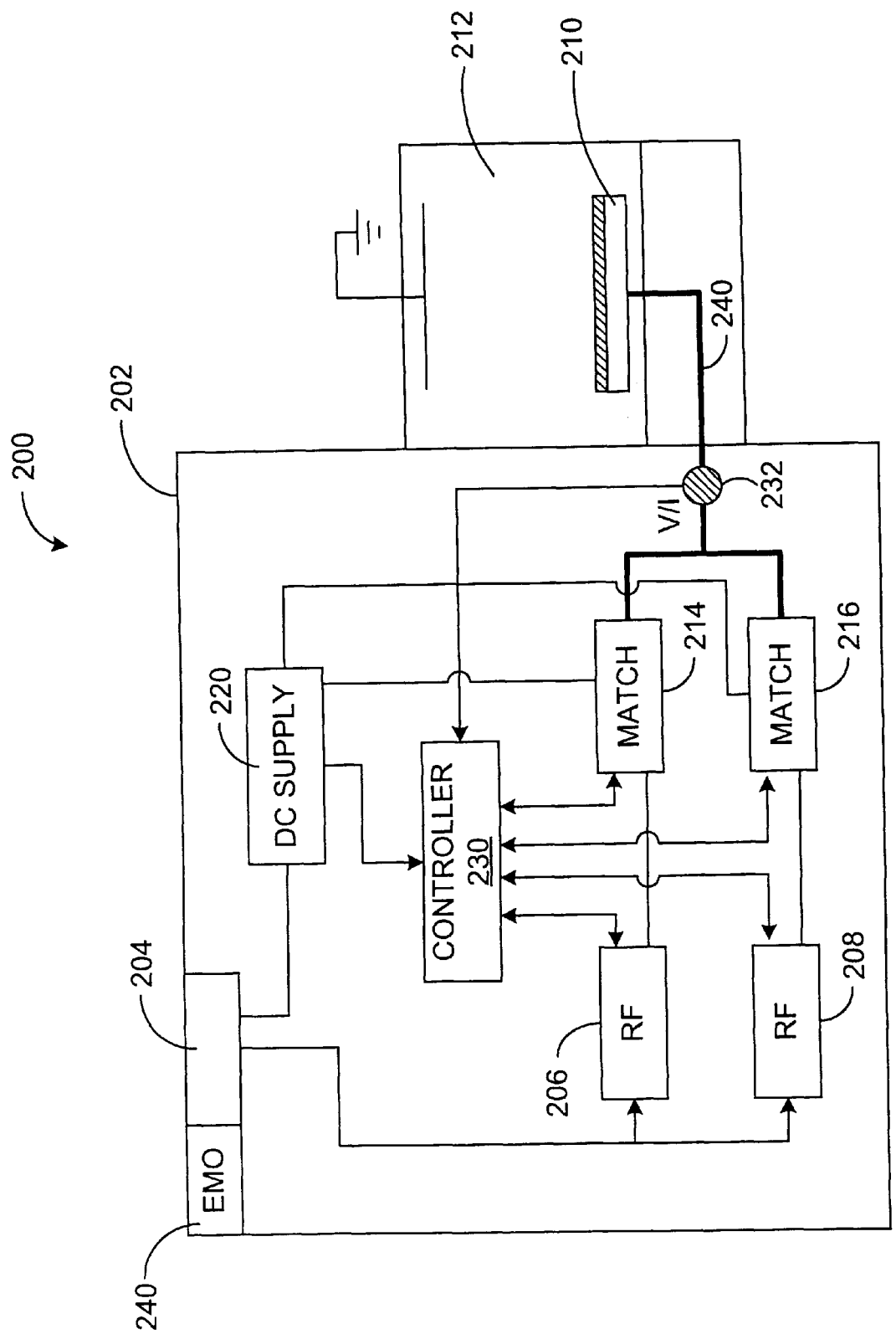
FIG. 2 illustrates, in accordance with one embodiment of the present invention, an integrated power module for a dual-frequencies, parallel plate plasma processing system.

To facilitate discussion of the features and advantages of the invention, reference may be made to the figures and discussions that follow. In FIG. 2, there is shown an integrated power module 200, representing the power delivery system for supplying the RF energy having dual frequencies to the electrodes of the parallel plate, multiple frequencies plasma processing chamber. With reference to FIG. 2, integrated power module 200 includes a system-wide EMI enclosure 202, typically formed of a metallic material to substantially contain the EMU radiation within the enclosure.

Within EMI enclosure 202, the major functional blocks of the power delivery system are enclosed. There is shown within EMI enclosure 202 a power distribution box 204, which has an input port to receive AC power from the distribution grid. In the example of FIG. 2, the AC power provided to power distribution box 204 may take the form of, for example, 3-phase 208 volts AC. As mentioned earlier, power distribution box 204 allows AC power to the various fictional blocks of the power delivery system to be shut down quickly in case of an emergency.

Power distribution box 204 includes at least three outputs for outputting AC power to the generators, the DC power supply, and to other AC loads associated with the plasma processing chamber. With referenced to FIG. 2, power distribution box 204 outputs AC power to RF generators 206 and 208. In one embodiment, the couplings between power distribution box 204 and RF generators 206 and 208 are accomplished through flexible conductive wirings.

RF generator 206 generates RF energy having a first frequency (27 MHz in the example of FIG. 2), which is subsequently provided to electrode 210 of plasma processing chamber 212 via a match network 214. Likewise RF generator 208 generates RF energy having a second frequency (2 MHz in the example of FIG. 2), which is subsequently provided to electrode 210 via a match network 216. The couplings between the RF generators and the match networks are preferably accomplished without the use of a coax cable and coax connectors to substantially eliminate the reliability issues associated with providing a high voltage/high current signal through the coax cable/connectors. It is possible to accomplish the couplings using simple conductors/straps due to the short distance involved in the integrated power module and the fact that these subsystems, along with their couplings, are substantially enclosed within the system-wide EMI enclosure.

Note that neither RF generator 206 nor RF generator 208 requires its own DC power supply. Instead, the control electronics associated with these RF generators are supplied DC power from the central DC power supply of integrated power module 200. In this manner, the redundancy of DC power supplies, which is seen in the example of prior art FIG. 1, is eliminated.

DC power supply 220 receives AC power from power distribution box 204 and generates the DC voltages necessary to operate the sensors, control electronics, and other DC loads of integrated power module 200 and plasma processing chamber 212. By way of example, DC power supply 220 may generate +5 volts, +/−12 volts, +/−15 volts, and/or +24 volts for the digital and analog circuits within integrated power module 200 and plasma processing chamber 212. Preferably DC power supply 220 represents the only DC power supply provided with integrated power module 200 for operating the various subsystems of integrated power module 200.

DC power supply 220 outputs DC power to DC loads external of integrated power module 200 (e.g., sensors, CPU, mass flow controllers, control electronics, and the like, associated with plasma processing chamber 212). Another output of DC power supply 220 couples to RF generator 206, RF generator 208, match network 214, and match network 216 to supply DC power to the control electronics therein. If there are other DC loads within integrated power module 200, these DC loads preferably obtain their DC voltages from DC power supply 220 as well. In this manner, the number of DC power supplies are drastically reduced, thereby advantageously reducing the footprint of the integrated power module.

In the implementation of FIG. 2, a controller 230 also receives DC power from DC power supply 220. Controller 230 represents the feedback control circuitry that receives a signal from a V/I probe 232 (e.g., an ammeter arrangement) indicative of the voltage or current supplied to electrode 210. Responsive to the signal from V/I probe 232, controller 230 issues commands to one or more of RF generator 206, RF generator 208, match network 214 and match network 216 to modulate the power output to account for losses in the conduction path between the output of the RF generators and electrode 210.

As mentioned, power distribution box 204 may also provide AC power, which may be one phase or three phase, to the various AC loads external of EMI enclosure 202. By way of example, these AC loads may include a turbo pump for evacuating the byproducts from the interior of plasma processing chamber 212, heaters, motors, and/or other AC loads associated with plasma processing chamber 212.

An EMO subsystem 240 is also provided within the EMI enclosure. Preferably, EMO subsystem 240 is associated with power distribution box 204 to permit AC power to DC power supply 220, the external AC loads, and the RF generators to be shut off quickly in case of an emergency. Because all the major functional blocks of the power delivery system is centralized within EMI enclosure 202, only one EMO subsystem is required, which is in contrast to the prior art situation of FIG. 1 wherein at least two EMO subsystems are provided.

In accordance with another aspect of the present invention, the output of match networks 214 and 216 are combined, and the combined dual-frequency signal is provided to only one of the electrodes of plasma processing chamber 212. To accomplish this, each of match networks 214 and 216 function to block the other frequency. One implementation of this direct coupling technique is discussed in connection with a subsequent FIG. 5 herein.

In the example of FIG. 2, the direct coupling of the outputs of match networks 214 and 216 is accomplished using a simple conductive strap 240, which carries the RF energy to electrode 210. In this manner, a coax cable and its associated coax connectors are not required, which advantageously obviates the reliability problems associated with using the coax cable/connector(s) to carry the high current/high voltage signal from the match networks to the electrode. Preferably, EMI enclosure 202 is coupled to plasma processing chamber 212 in a manner so as to allow the entire length of the conductive strap between the match network outputs and electrode 210 to be always enclosed within some form of EMI enclosure. By way of example, EMI enclosure 202 may be placed in direct contact with the enclosure of plasma processing chamber 212 to allow the conductive strap to always remain within one of the enclosures for its entire length between the match network outputs and electrode 210.

Figure 3:
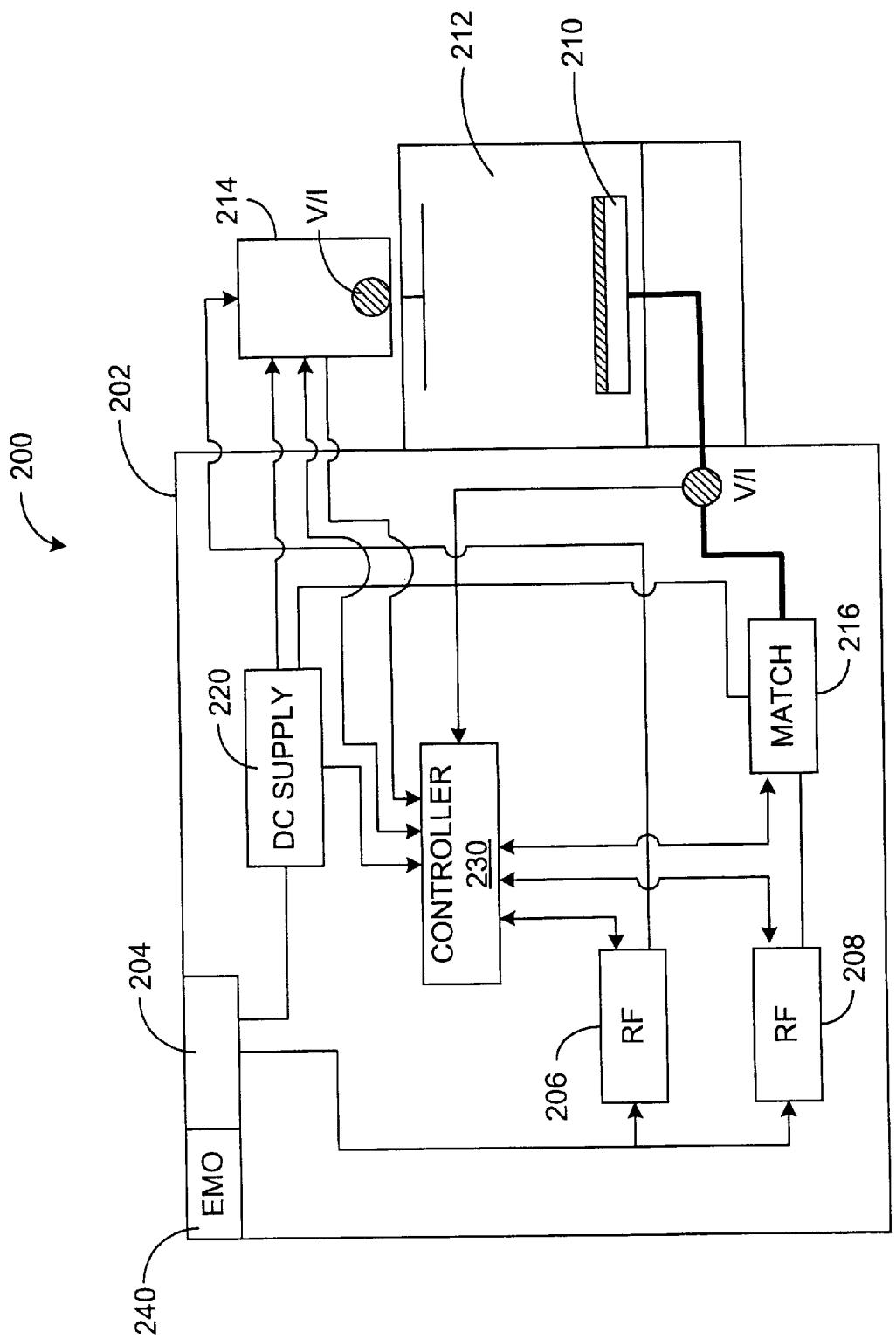
FIG. 3 illustrates, in accordance with another embodiment of the present invention, an integrated power module for another dual-frequencies plasma processing system.

If desired, the outputs from the match network may be provided separately to the electrodes of the plasma processing chamber. The coupling between each match network output and its associated electrode may be accomplished by a conductive strap or via a coax cable, if desired. FIG. 3 illustrates the situation wherein RF energy from one of the match networks is provided to one electrode via a coax cable, while RF energy from the output of the other match network is provided to the other electrode via a conductive strap. This implementation is particularly useful for inductively-coupled type plasma processing systems, such as the TCP™-brand inductively coupled plasma processing systems available from Lam Research Corporation of Fremont, Calif. Again, a V/I probe may be provided at the output of each match network to facilitate feedback control of the output of the RF generators and/or the settings of the match networks.

Note that although only one chamber 212 is illustrated in FIGS. 2 & 3 to simplify the drawing, the inventive IPM may be configured to work with any number of chambers in the cluster tool's module. By way of example, if multiple chambers 212 are provided per module of the cluster tool, the multiple sets of RF generators 206 and 208 that are provided with the multiple chambers may, in one embodiment, be connected a single power distribution box 204 of IPM 200, thereby enabling a single power distribution box 204 (and EMO subsystem 240) to service the needs of multiple sets of RF generators 206 and 208 that are provided with the multiple chambers. Alternatively or additionally, the multiple sets of RF generators (206 and 208), match networks (214 and 216), and V/I probes that are provided with the multiple chambers may, in one embodiment, be in communication with a single controller 230 of the IPM, thereby enabling a single controller 230 to service the needs of multiple sets of RF generators (206 and 208), match networks (214 and 216) and VI probes that are provided with the multiple chambers. Alternatively or additionally, the multiple sets of RF generators (206 and 208) and match networks (214 and 216) that are provided with the multiple chambers may, in one embodiment, receive DC power from a single DC supply 220 of the IPM, thereby enabling a single DC supply 220 to service the needs of multiple sets of RF generators (206 and 208) and match networks (214 and 216) that are provided with the multiple chambers. In this manner, although the power distribution box 204 (and EMO subsystem 240) and/or DC supply 220 and/or controller 230 of IPM 200 may be need to be scaled in terms of capacity to service the needs of the multiple chambers of the cluster tool's module, the need for multiple power distribution boxes, EMO subsystems, DC supplies, and/or controllers (as well as their enclosures and interconnects) are advantageously eliminated.

Figure 4:
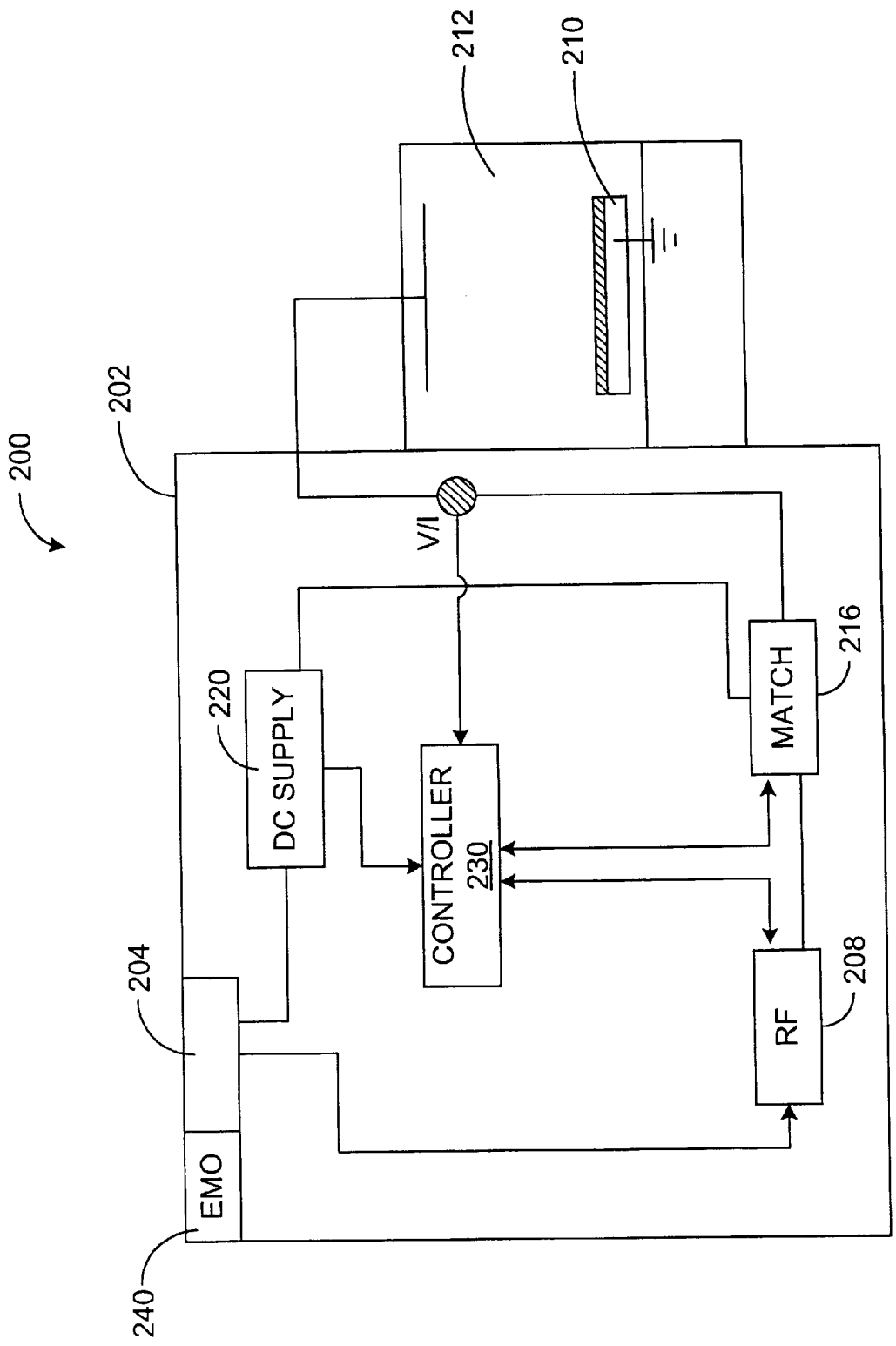
FIG. 4 illustrates, in accordance with one embodiment of the present invention, an integrated power module for a single frequency plasma processing system.

For systems which have only one power electrode and requires only a single frequency for operation, one of the two sets of generator/match of FIG. 3 may be eliminated. FIG. 4 illustrates this implementation wherein only one RF generator and one match network are required within EMI enclosure 202. With reference to the implementation of FIG. 4, where a cluster tool module having multiple chambers is involved, it is preferred that the multiple sets of RF supply 208, match network 216, and V/I probe that are provided with the multiple chambers may all be serviced by a single power distribution box 204 (and EMO subsystem 240) and/or a single DC supply 220 and/or a single controller 230. As discussed above, although such cluster tool arrangement may require the capacity of each component to be scaled up in term of capacity, the need for multiple power distribution boxes, EMO subsystems, DC supplies, and/or controllers (as well as their enclosures and interconnects) are advantageously eliminated.

Figure 5:
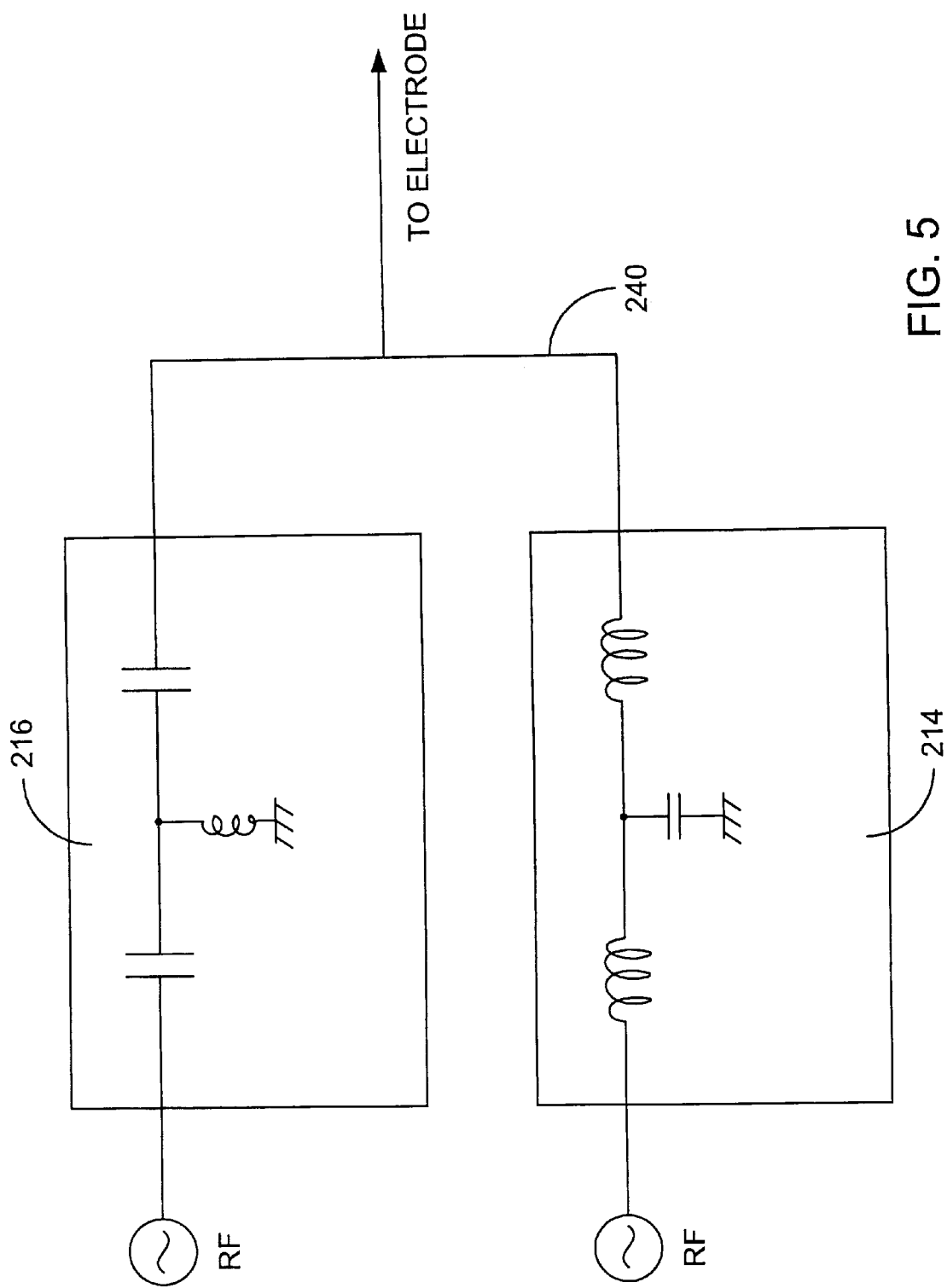
FIG. 5 illustrates, in accordance with one aspect of the present invention, a technique for directly coupling match network outputs together.

FIG. 5 illustrates, in accordance with one embodiment of the present invention, the technique of tying the outputs of the match networks together so that only one conductor is required to supply both RF frequencies to the plasma within the plasma processing chamber. With reference to FIG. 5, match network 214 functions as a low pass filter that permits RF frequency of 2 MHz to pass through. Match network 216 functions as a high pass filter that permits 27 MHz frequency pass through. Neither match network permits the other frequency to pass through, thereby effectively isolating the RF generators from one another.

The outputs of match networks 214 and 216 are tied together by a conductive strap that has sufficient capacity to carry the high current/high voltage signal to the electrode for igniting and/or sustaining the plasma. In accordance with one aspect of the present invention, the combined signal carried by the strap 240 is coupled to only one electrode of the dual frequencies plasma processing chamber. The other electrode is coupled to ground. Since only one conductive strap is required, the strap may be shortened such that there will be EMI shielding provided by the enclosure of integrated power module 200 and/or the enclosure of the plasma processing chamber for its entire length. Also, the diplexer of the prior art configuration may be eliminated, resulting in less complexity and cost.

As can be appreciated from the foregoing, the inventive design approach advantageously reduces the component count of the power module, which reduces the amount of raw materials and energy required to construct the hardware of the integrated power module as well as to operate the integrated power module during its service life. These reductions also advantageously permit the IPM to be employed in a more environmentally-friendly manner, thereby lowering the costs associated with manufacturing, operating and eventually disposing of IPM components (at the end of their useful life).

While this invention has been described in terms of several preferred embodiments, there are alterations, permutations, and equivalents which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. A power delivery system for providing energy to sustain a plasma in a plasma processing chamber configured for processing substrates, comprising:

a metallic enclosure having an input port, a first output port, a second output port, and a third output port;

a power distribution box disposed within said enclosure, said power distribution box including a first AC input port for receiving AC power from external of said metallic enclosure through said input port and for providing AC power to AC loads external to said metallic enclosure via said first output port;

a DC power supply electrically coupled to said power distribution box, said DC power supply being configured to receive said AC power from said power distribution box and to output DC power, said DC power supply being disposed within said metallic enclosure, said DC power being supplied to DC loads external of said metallic enclosure via said second output port;

a first RF generator electrically coupled to said power distribution box to receive said AC power, said first RF generator being coupled with said DC power supply to receive said DC power, said first RF generator being disposed within said metallic enclosure; and a first match network electrically coupled with an output of said first RF generator to receive RF energy from said first RF generator, said first match network having a first match network output for providing first matched RF energy to a first electrode of said plasma processing chamber via said third output port, said first match network being disposed within said metallic enclosure, wherein no other RF generator associated with said plasma processing chamber exists outside said metallic enclosure.

2. The power delivery system of claim 1 further comprising:

a second RF generator electrically coupled to said power distribution box to receive said AC power, said second RF generator being coupled with said DC power supply to receive said DC power, said second RF generator being disposed within said metallic enclosure;

a second match network electrically coupled with an output of said second RF generator to receive RF energy from said second RF generator, said second match network having a second match network output for providing second matched RF energy to said first electrode via said third output port, said second match network being coupled with said DC power supply to receive said DC power, said second match network being disposed within said metallic enclosure.

3. The power delivery system of claim 2 wherein said first match network output and said second match network output are directly coupled via a conductive strap, wherein both said first matched RF energy and said second matched RF energy are provided to said first electrode via said conductive strap.

4. The power delivery system of claim 3 wherein a coupling between said first RF generator and said first match network is accomplished without a coax cable.

5. The power delivery system of claim 1 wherein a coupling between said first RF generator and said first match network is accomplished without a coax cable connector.

6. The power delivery system of claim 1 wherein said DC loads external of said metallic enclosure that receives said DC power via said second output port include a pressure sensor for sensing pressure within said plasma processing chamber.

7. The power delivery system of claim 1 wherein said DC loads external of said metallic enclosure that receives said DC power via said second output port include control electronics for said plasma processing chamber.

8. The power delivery system of claim 1 wherein said AC loads external of said metallic enclosure that receives said AC power via said first output port include a turbo pump for evacuating byproduct gases from said plasma processing chamber.

9. The power delivery system of claim 1 further comprising:
a second RF generator electrically coupled to said power distribution box to receive said AC power, said second RF generator being coupled with said DC power supply to receive said DC power, said second RF generator being disposed with in said metallic enclosure;
a second match network electrically coupled with an output of said second RF generator to receive RF energy from said second RF generator, said second match network having a second match network output for providing second matched RF energy to a second electrode of said plasma processing chamber via said third output port, said second match network being coupled with said DC power supply to receive said DC power, said second match network being disposed within said metallic enclosure.

10. The power delivery system of claim 1 further including an emergency off (EMO) subsystem disposed within said metallic enclosure, wherein no other EMO subsystem associated with said power delivery system exists downstream of said input port.

11. The power delivery system of claim 1 further including an emergency off (EMO) subsystem disposed within said metallic enclosure, wherein no other EMO subsystem associated with said power delivery system exists outside of said metallic enclosure.

12. A power delivery system for providing energy to an electrode of a plasma processing chamber configured for processing substrates, comprising:
EMI shielding means for enclosing hardware of said power delivery system within an EMI enclosure, said EMI shielding means having an input port, a first output port, a second output port, and a third output port;
power distributing means disposed within said enclosure for receiving AC power from external of said EMI shielding means through said input port and for providing AC power at least to AC loads external to said EMI shielding means via said first output port;
a DC power supply electrically coupled to said power distributing means, said DC power supply being configured to receive said AC power from said power distributing means and to output DC power, said DC power supply being disposed within said EMI shielding means, said DC power being supplied to DC loads external of said EMI shielding means via said second output port;
a first energy generation means for generating said energy required by said electrode, said first energy generation means being electrically coupled to said power distributing means to receive said AC power, said first energy generation means being coupled with said DC power supply to receive said DC power, said first energy generation means being disposed within said EMI shielding means wherein no other energy generation means associated with said plasma processing chamber exists outside said EMI shielding means.

13. The power delivery system of claim 12 further comprising:
a second energy generation means for generating said energy required by said electrode, said second energy generation means being electrically coupled to said power distributing means to receive said AC power, said second energy generation means being coupled with said DC power supply to receive said DC power, said second energy generation means being disposed within said EMI shielding means.

14. The power delivery system of claim 13 wherein each of said first energy generation means and said second energy generation means includes a RF generator and a match network.

15. The power delivery system of claim 14 wherein a coupling between said RF generator and said match network is accomplished without a coax cable.

16. The power delivery system of claim 14 wherein a coupling between said RF generator and said match network is accomplished without a coax cable connector.

17. The power delivery system of claim 12 wherein said DC loads external of said EMI shielding means that receives said DC power via said second output port include a pressure sensor for sensing pressure within said plasma processing chamber.

18. The power delivery system of claim 12 wherein said DC loads external of said EMI shielding means that receives said DC power via said second output port include control electronics for said plasma processing chamber.

19. The power delivery system of claim 12 wherein said AC loads external of said EMI shielding means that receives said AC power via said first output port include a turbo pump for evacuating byproduct gases from said plasma processing chamber.

20. The power delivery system of claim 12 further comprising:
a second energy generation means for generating said energy required by another electrode of said plasma processing chamber, said second energy generation means being electrically coupled to said power distributing means to receive said AC power, said second energy generation means being coupled with said DC power supply to receive said DC power, said second energy generation means being disposed within said EMI shielding means.

21. A method for providing energy to sustain plasma in a plasma processing chamber configured for processing substrates, comprising:

providing a metallic enclosure having an input port, a first output port, a second output port, and a third output port;

placing a power distribution box within said enclosure, said power distribution box including a first AC input port for receiving AC power from external of said metallic enclosure through said input port and for providing AC power to AC loads external to said metallic enclosure via said first output port;

electrically coupling a DC power supply to said power distribution box, said DC power supply being configured to receive said AC power from said power distribution box and to output DC power, said DC power supply being disposed within said metallic enclosure, said DC power being supplied to DC loads external of said metallic enclosure via said second output port;

electrically coupling a first RF generator to said power distribution box to receive said AC power, said first RF generator being coupled with said DC power supply to receive said DC power, said first RF generator being disposed within said metallic enclosure; and electrically coupling a first match network with an output of said first RF generator to receive RF energy from said first RF generator, said first match network having a first match network output for providing first matched RF energy to an electrode via said third output port, said first match network being disposed within said metallic enclosure, wherein no other RF generator associated with said plasma processing chamber exists outside said metallic enclosure.

22. The method of claim 21 further comprising:

electrically coupling a second RF generator to said power distribution box to receive said AC power, said second RF generator being coupled with said DC power supply to receive said DC power, said second RF generator being disposed within said metallic enclosure;

electrically coupling a second match network with an output of said second RF generator to receive RF energy from said second RF generator, said second match network having a second match network output for providing second matched RF energy to said electrode via said third output port, said second match network being coupled with said DC power supply to receive said DC power, said second match network being disposed within said metallic enclosure.

23. The method of claim 22 further comprising directly coupling said first match network output with said second match network output by a conductive strap, wherein both said first matched RF energy and said second matched RF energy are provided to said electrode via said conductive strap.

24. The method of claim 21 wherein said coupling between said first RF generator and said first match network is accomplished without a coax cable.

25. A power delivery system for providing energy to sustain a plasma in a plasma processing chamber configured for processing substrates, comprising:

a metallic enclosure having an input port, a first output port, a second output port, and a third output port;

a power distribution box disposed within said enclosure, said power distribution box including a first AC input port for receiving AC power from external of said metallic enclosure through said input port and for providing AC power to AC loads external to said metallic enclosure via said first output port;

a DC power supply electrically coupled to said power distribution box, said DC power supply being configured to receive said AC power from said power distribution box and to output DC power, said DC power supply being disposed within said metallic enclosure, said DC power being supplied to DC loads external of said metallic enclosure via said second output port;

a first RF generator electrically coupled to said power distribution box to receive said AC power, said first RF generator being coupled with said DC power supply to receive said DC power, said first RF generator being disposed within said metallic enclosure; and a first match network electrically coupled with an output of said first RF generator to receive RF energy from said first RF generator, said first match network having a first match network output for providing first matched RF energy to said plasma via said third output port, said first match network being disposed within said metallic enclosure;

a second RF generator electrically coupled to said power distribution box to receive said AC power, said second RF generator being coupled with said DC power supply to receive said DC power, said second RF generator being disposed within said metallic enclosure; and a second match network electrically coupled with an output of said second RF generator to receive RF energy from said second RF generator, said second match network having a second match network output for providing second matched RF energy to said plasma via said third output port, said second match network being coupled with said DC power supply to receive said DC power, said second match network being disposed within said metallic enclosure, wherein no other RF generator associated with said plasma processing chamber exists outside said metallic enclosure.

26. The power delivery system of claim 25 further including an emergency off (EMO) subsystem disposed within said metallic enclosure, wherein no other EMO subsystem associated with said power delivery system exists outside of said metallic enclosure.

27. A power delivery system for providing energy to sustain plasma in a plurality of plasma processing chambers of a cluster tool module, said cluster tool module being configured for processing semiconductor substrates, comprising:

a metallic enclosure having an input port, a first output port, a second output port, and a third output port;

a power distribution box disposed within said enclosure, said power distribution box including a first AC input port for receiving AC power from external of said metallic enclosure through said input port and for providing AC power to AC loads external to said metallic enclosure via said first output port;

a DC power supply electrically coupled to said power distribution box, said DC power supply being configured to receive said AC power from said power distribution box and to output DC power, said DC power supply being disposed within said metallic enclosure, said DC power being supplied to DC loads external of said metallic enclosure via said second output port; and a plurality of RF generators electrically coupled to said power distribution box to receive said AC power, said plurality of RF generators being coupled with said DC power supply to receive said DC power, said plurality of RF generator being disposed within said metallic enclosure and configured to provide RF power to said plurality of plasma processing chambers.

28. The power delivery system of claim 27 further comprising a plurality of match networks, each of said plurality of match networks being electrically coupled with said DC power supply and a respective one of said plurality of RF generators to receive RF energy from said plurality of said RF generators, said each of said plurality of match networks being associated with one of said plurality of plasma processing chambers and having a match network output for providing matched RF energy to an electrode of said one of said plurality of plasma processing chambers.

29. A method for providing energy to sustain plasma in a plurality of plasma processing chambers of a cluster tool module that is configured for processing semiconductor substrates, comprising:

providing a metallic enclosure having an input port, a first output port, a second output port, and a third output port;

placing a power distribution box within said enclosure, said power distribution box including a first AC input port for receiving AC power from external of said metallic enclosure through said input port and for providing AC power to AC loads external to said metallic enclosure via said first output port;

electrically coupling a DC power supply to said power distribution box, said DC power supply being configured to receive said AC power from said power distribution box and to output DC power, said DC power supply being disposed within said metallic enclosure, said DC power being supplied to DC loads external of said metallic enclosure via said second output port; and electrically coupling a plurality of RF generators to said power distribution box to receive said AC power, said plurality of RF generators being coupled with said DC power supply to receive said DC power, said plurality of RF generators being disposed within said metallic enclosure and configured to provide RF power to said plurality of plasma processing chambers.

30. The method of claim 29 further comprising:

electrically coupling each of a plurality of match networks with said DC power supply and a respective one of said plurality of RF generators, said each of said plurality of match networks being associated with one of said plurality of plasma processing chambers and having a match network output for providing matched RF energy to an electrode of said one of said plurality of plasma processing chambers.

* * * * *